United States Patent [19]

Hara et al.

[11] 4,339,452
[45] Jul. 13, 1982

[54] METHODS OF INHIBITING BLOOD PLATELET AGGREGATION WITH CAROVERINE FUMARATE

[75] Inventors: Hiroto Hara, Machida; Akihiro Narimatsu, Yokohama, both of Japan

[73] Assignee: Medichemie AG, Ettingen, Switzerland

[21] Appl. No.: 218,284

[22] Filed: Dec. 19, 1980

[30] Foreign Application Priority Data

Dec. 28, 1979 [JP]  Japan ................................ 54/173249

[51] Int. Cl.³ .......................................... A61K 31/495
[52] U.S. Cl. .................................................. 424/250
[58] Field of Search ......................................... 424/250

[56] References Cited

FOREIGN PATENT DOCUMENTS 50-160417  12/1975  Japan .

OTHER PUBLICATIONS

Ishida et al.—Brit. J. of Pharmacology, vol. 71 (1980), pp. 343–348.

Primary Examiner—Sam Rosen
Attorney, Agent, or Firm—Yount & Tarolli

[57] ABSTRACT

Caroverine fumarate has an inhibitory effect on platelet aggregation, and exhibits the beneficial effect of increasing coronary blood flow, especially in coronary arteries, and thus is specifically suitable in applications for ischemic heart diseases.

11 Claims, 6 Drawing Figures

METHODS OF INHIBITING BLOOD PLATELET AGGREGATION WITH CAROVERINE FUMARATE

BACKGROUND OF THE INVENTION

At present, platelet aggregation inhibitors such as aspirin have been found to be clinically effective. However, there is a continuing desire for the development of new platelet aggregation inhibitors paricularly those having certain additional effects.

It has been known that a compound of the formula 1-(2-diethylaminoethyl)-3-(p-methoxybenzyl)-1,2,-dihydroquinoxaline-2-one (hereinafter referred to as "caroverine") fumarate (this salt is hereinafter referred to as "caroverine fumarate".) increases blood flow by dilating arterial vessels, and that it has a spasmolytic effect (cr. Japanese Patent Laid-open (KOKAI) No. 160417/1975, etc.).

Caroverine fumarate is a known compound and is produced, for example, by a process which is described in the said Japanese Patent Application Laid-open.

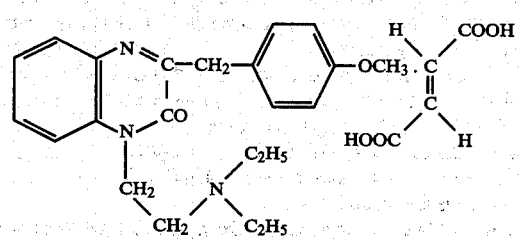

GENERAL DESCRIPTION OF THE INVENTION

Upon various studies under the above described circumstances, the inventors of this invention have found that caroverine fumarate has an inhibitory effect on platelet aggregation, and they have found that it is suitable for clinical applications. Furthermore, they have found that caroverine fumarate in such application exhibits the beneficial effect of increasing coronary blood flow and thus is specifically suitable in applications for ischemic heart diseases.

Thus the present invention concerns the use of caroverine fumarate for platelet aggregation inhibition and medicine containing caroverine fumarate as an active ipgredient.

Caroverine fumarate can be administered alone or in combination with pharmaceutically acceptable carriers, the proportion of which is determined by chosen route of administration and standard pharmaceutical practice.

The dosage administered will be dependent upon the age, health, weight and condition of illness of the recipient, kind of concurrent treatment if any, frequency of treatment, and the nature of the effect desired. The therapeutic dosage is generally 0.3-2 mg/kg parenterally, 2-10 mg/kg orally per day.

Caroverine fumarate can be employed in dosage forms such as tablets, capsules, powder packets, or liquid solutions, or elixirs, for oral administration, or sterile liquid formulations such as solutions or suspensions for parenteral use. In such compositions, besides the active ingredient of this invention, the composition will contain a solid or liquid non-toxic pharmaceutical carrier for the active ingredient. In one embodiment of a composition, the solid carrier can be a capsule of the ordinary gelatin type. In another embodiment, the active ingredient can be tableted or granulated with or without adjuvants, or put into powder packets. The vehicles used in the above compositions are water; gelatin; saccharides such as lactose and glucose; starches such as corn, wheat, rice and arrowroot; fatty acids such as stearic acid; salts of fatty acids such as calcium stearate and magnesium stearate; talc; vegetable oil; alcohols such as stearyl alcohol and benzyl alcohol; gum; polyalkylene glycols.

These capsules, tablets, granules and powders will generally contain from about 5% to about 100% and preferably from 25% to 100% by weight of active ingredient.

The pharmaceutical carrier can be a liquid such as water and oils, including those of petroleum, animal, vegetable or synthetic origin, such as peanut oil, soybean oil, mineral oil, sesame oil, and the like. In general, water saline, aqueous dextrose and related sugar solutions, and glycols such as ethylene glycol, propylene glycol and polyethylene glycol are preferred liquid carriers.

Caroverine fumarate may be injected parenterally, that is, intramuscularly, intravenously or subcutaneously. For parenteral administration, caroverine fumarate may be used in the form of sterile solutions containing other solutes, for example, sufficient saline or glucose to make the solution isotonic.

Examples of the suitable solvents for injection are sterile water, lidocaine hydrochloride solution (for intramuscular injection), water saline, glucose solution for intravenous injection and solution including electrolytes for intravenous injection. These solutions for injection will generally contain from about 0.5% to about 20% and preferably from about 1 to about 10% by weight of active ingredient.

Oral administration can be in a suitable suspension or syrup, in which the active ingredient normally will constitute from about 0.5 to 10% by weight. The pharmaceutical carrier in such composition can be a watery vehicle such as an aromatic water, a syrup or a pharmaceutical muculage.

Summarizing, it has to be stated that caroverine fumarate has an inhibitory effect on platelet aggregation and an increasing effect on blood flow in arteries, particularly in coronary arteries. Consequently, caroverine fumarate is useful as a therapeutic and preventive agent for ischemic heart diseases such as angina pectoris, myocardial infarction and the like. Thus the invention pertains to methods of curing diseases or assisting in medical operations as well with the aid of caroverine fumarate as well as to medicine for curing such diseases containing caroverine fumarate as an active ingredient.

The marks of o and - indicate the points of administration.

DETAILED DESCRIPTION OF THE INVENTION

The following examples are given to further illustrate the present invention, but they are not intended to limit the invention thereto as long as the invention falls within the scope defined by the claims.

EXAMPLE 1

An inhibitory effect on platelet aggregation

Platelet-rich plasma was prepared from citrated blood of rabbits. An inhibitory effect on platelet aggregation induced by bovine Achilles tendon collagen was tested by turbidimetry.

Figure 1:
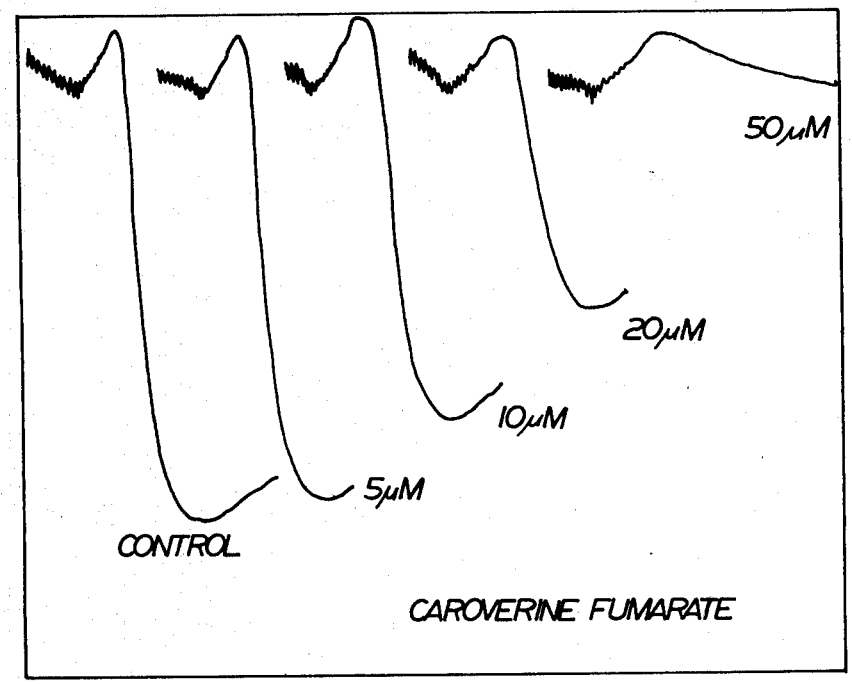
FIGS. 1 to 3 illustrate the relationship between dose and action in Example 1.
Figure 2:
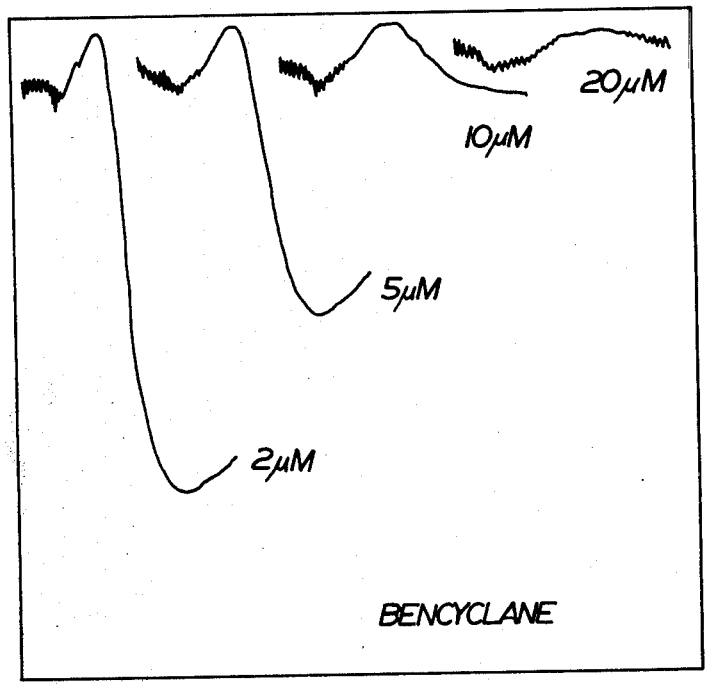
Figure 3:
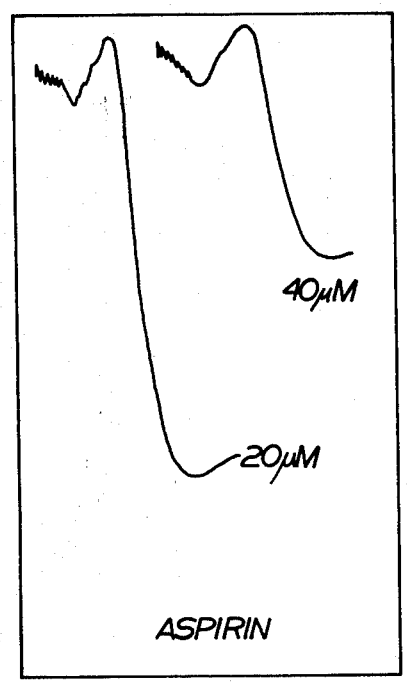

Caroverine fumarate, and bencyclane fumarate and aspirin both for comparison were used. FIGS. 1 to 3 illustrate typical results. Each of these figures is a multiple-record consisting of several diagrams of a turbidimetrically measured value representing the degree of platelet aggregation over the aggregating-reaction time, each diagram in the multiple-record having been obtained for the dose of aggregation inhibiting agent indicated therebelow. The measured values represented along the ordinate of the diagrams as well as the ordinate axis itself are not shown, since the diagrams have been obtained as record photographs by experiment. Accordingly the abscissa axis represents the reaction time after administration.

Records of the same type have been obtained in experiments carried out with human blood. Thus the utility of caroverine fumarate for inhibiting platelet aggregation in human blood blood has also been shown.

REFERENCE EXAMPLE 1

Effects of caroverine fumarate on coronary sinus outflow

Figure 4:
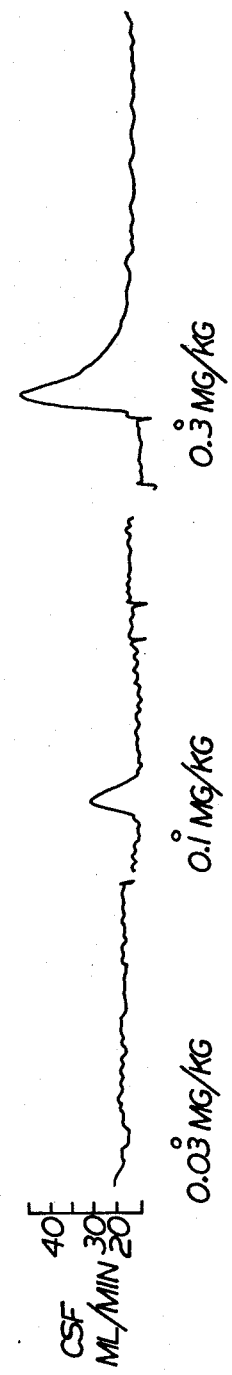
FIGS. 4 to 6 illustrate the relationship between dose and action on coronary sinus outflow (CSF) in Reference Example 1.
Figure 5:
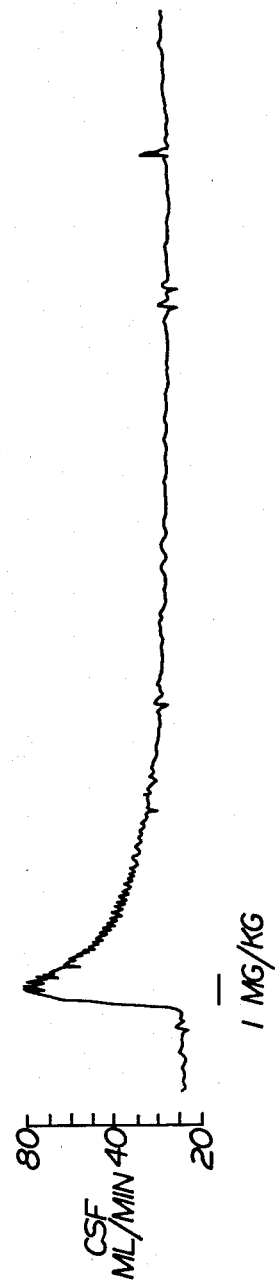
Figure 6:
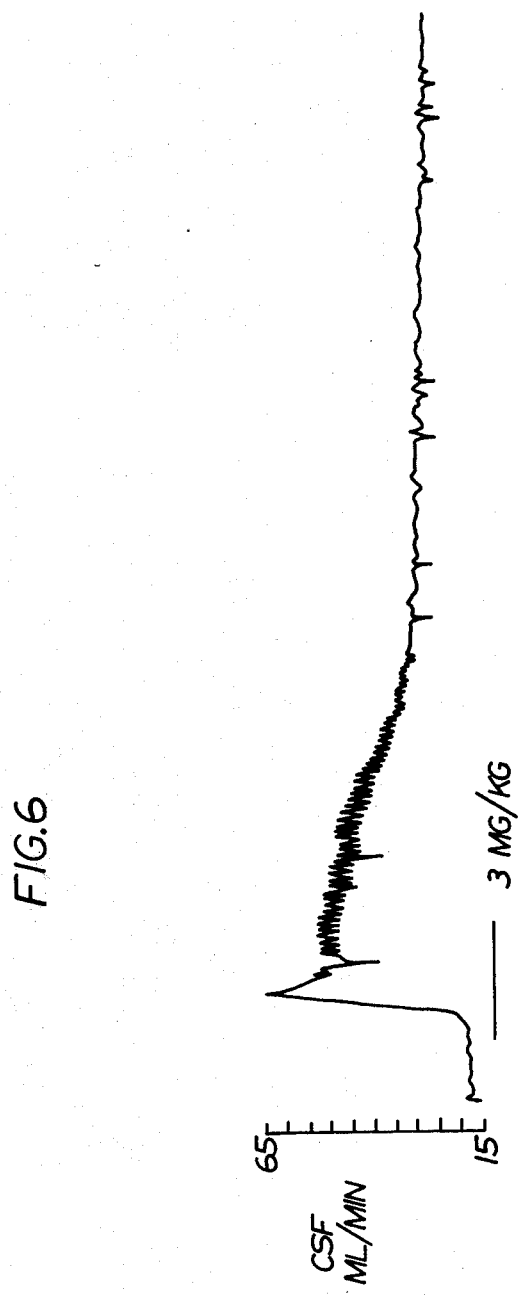

CSF are measured in dogs and the results are shown in FIGS. 4 to 6. CSF was measured by a method which is described in Clin. Pharmacol. Physiol., 5, 107–115, 1978, Australia. The diagrams are photographs of CSF-records over time.

REFERENCE EXAMPLE 2

Acute toxicity in male mice

|  | $LD_{50}$ (mg/kg) |
| --- | --- |
| Intravenous Administration | 39 |
| Intraperitoneal Administration | 138 |
| Oral Administration | 800 |

We claim:

1. A method of inhibiting blood platelet aggregation in a patient requiring such treatment, comprising administering to said patient a therapeutic dosage of a platelet aggregation inhibiting substance containing caroverine fumarate as an active ingredient.

2. A method as set forth in claim 1, wherein said therapeutic dosage of caroverine fumarate constitutes 0.3–2 mg/kg of patient weight if administered parenterally, and 2–10 mg/kg of patient weight if administered orally.

3. A method as set forth in claim 1, wherein said caroverine fumarate is administered in a pharmaceutically acceptable carrier.

4. A method as set forth in claim 3 wherein the composition is in a solid state and said pharmaceutically acceptable carrier is selected from a group of substances consisting of gelatin, saccharides, starches, fatty acids, salts of fatty acids, talc, vegetable oil, alcohols, gum and polyalkylene glycols.

5. A method as set forth in claim 1 wherein the composition generally contains from about 5% to about 100% by weight caroverine fumarate.

6. A method as set forth in claim 1, wherein the composition contains from 28% to about 100% by weight caroverine fumarate.

7. A method as set forth in claim 3, wherein the composition is in a liquid state and said pharmaceutically acceptable carrier is selected from a group of substances consisting of water and oil, said oil being of petroleum, animal, vegetable or synthetic origin.

8. A method as set forth in claim 3, wherein the composition is in the form of sterile solution when administered parenterally.

9. A method as set forth in claim 8, wherein the solution comprises as a solvent, sterile water, lidocaine hydrochloride solution, water saline, glucose solution, or a solution including an electrolyte.

10. A method as set forth in claim 8, wherein the sterile solution contains caroverine fumarate from about 0.5% to about 20% by weight.

11. A method as set forth in claim 8, wherein the sterile solution contains from 1% to 10% by weight caroverine fumarate.

UNITED STATES PATENT AND TRADEMARK OFFICE
CERTIFICATE OF CORRECTION

PATENT NO. : 4,339,452
DATED : July 13, 1982
INVENTOR(S) : Hiroto Hara et al.

It is certified that error appears in the above-identified patent and that said Letters Patent are hereby corrected as shown below:

Column 4, line 30 change "28%" to --25%--.

Signed and Sealed this

Fifth Day of October 1982

[SEAL]

Attest:

GERALD J. MOSSINGHOFF

Attesting Officer    Commissioner of Patents and Trademarks